(12) United States Patent
Jackson

(10) Patent No.: US 12,369,950 B2
(45) Date of Patent: Jul. 29, 2025

(54) BONE ANCHOR ASSEMBLIES WITH INTERCHANGEABLE AND DIFFERENT LOCKING THREADED CLOSURES

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 77 days.

(21) Appl. No.: 18/438,270

(22) Filed: Feb. 9, 2024

(65) Prior Publication Data

US 2024/0299064 A1 Sep. 12, 2024

Related U.S. Application Data

(60) Continuation of application No. 18/332,665, filed on Jun. 9, 2023, now Pat. No. 11,925,390, which is a continuation of application No. 16/380,509, filed on Apr. 10, 2019, now Pat. No. 11,707,298, which is a division of application No. 15/389,296, filed on Dec. 22, 2016, now abandoned, which is a continuation of application No. 12/661,042, filed on Mar. 10, 2010, now abandoned, which is a continuation-in-part of application No. 12/584,980, filed on Sep. 15, 2009, now Pat. No. 10,729,469, and a continuation-in-part of application No. 12/229,207, filed on Aug. 20, (Continued)

(51) Int. Cl.
*A61B 17/70* (2006.01)
*A61B 17/00* (2006.01)

(52) U.S. Cl.
CPC ...... *A61B 17/7022* (2013.01); *A61B 17/7008* (2013.01); *A61B 17/702* (2013.01); *A61B 17/7029* (2013.01); *A61B 17/7031* (2013.01);

*A61B 17/7032* (2013.01); *A61B 17/7035* (2013.01); *A61B 2017/00862* (2013.01); *A61B 2017/00933* (2013.01); *A61B 2017/00955* (2013.01); *Y10T 29/49826* (2015.01)

(58) Field of Classification Search
CPC .............. A61B 17/702; A61B 17/7032; A61B 17/7034; A61B 17/7035; A61B 17/7037
See application file for complete search history.

(56) References Cited

U.S. PATENT DOCUMENTS

| 7,828,825 | B2 * | 11/2010 | Bruneau | A61B 17/7031 606/259 |
| 2006/0247635 | A1 * | 11/2006 | Gordon | A61F 2/4405 606/279 |
| 2009/0088799 | A1 * | 4/2009 | Yeh | A61B 17/7083 606/264 |

* cited by examiner

*Primary Examiner* — Ellen C Hammond
(74) *Attorney, Agent, or Firm* — Polsinelli PC

(57) ABSTRACT

A receiver assembly for capturing an elongate rod in a receiver of a bone anchor includes the receiver, a first threaded closure, and a second threaded closure. The receiver includes an upper portion that defines a first channel, interior surfaces that have helically wound thread, and a lower pressure insert that can be positioned within the first channel and has upright arms. Each of the first threaded closure and the second threaded closure have a cylindrical body with an external surface having continuous helically wound thread that can rotatably mate with the helically wound receiver thread. The first threaded closure and the second threaded closure are interchangeable for different locking configurations in the receiver assembly. The first threaded closure has a downward protrusion that can compressively engage the elongate rod. The second threaded closure has a bottom surface that can compressively engage the upright arms of the lower pressure insert.

5 Claims, 7 Drawing Sheets

Related U.S. Application Data 2008, now Pat. No. 8,353,932, and a continuation-in-part of application No. 12/148,465, filed on Apr. 18, 2008, now Pat. No. 10,258,382, said application No. 12/229,207 is a continuation-in-part of application No. 11/894,001, filed on Aug. 17, 2007, now Pat. No. 8,292,926, said application No. 12/661,042 is a continuation-in-part of application No. 11/328,481, filed on Jan. 9, 2006, now Pat. No. 7,862,587.

(60) Provisional application No. 61/210,058, filed on Mar. 13, 2009, provisional application No. 61/192,312, filed on Sep. 17, 2008, provisional application No. 60/994,083, filed on Sep. 17, 2007, provisional application No. 60/927,111, filed on May 1, 2007, provisional application No. 60/851,353, filed on Oct. 12, 2006, provisional application No. 60/736,112, filed on Nov. 10, 2005, provisional application No. 60/728,912, filed on Oct. 21, 2005, provisional application No. 60/725,445, filed on Oct. 11, 2005, provisional application No. 60/722,300, filed on Sep. 30, 2005.

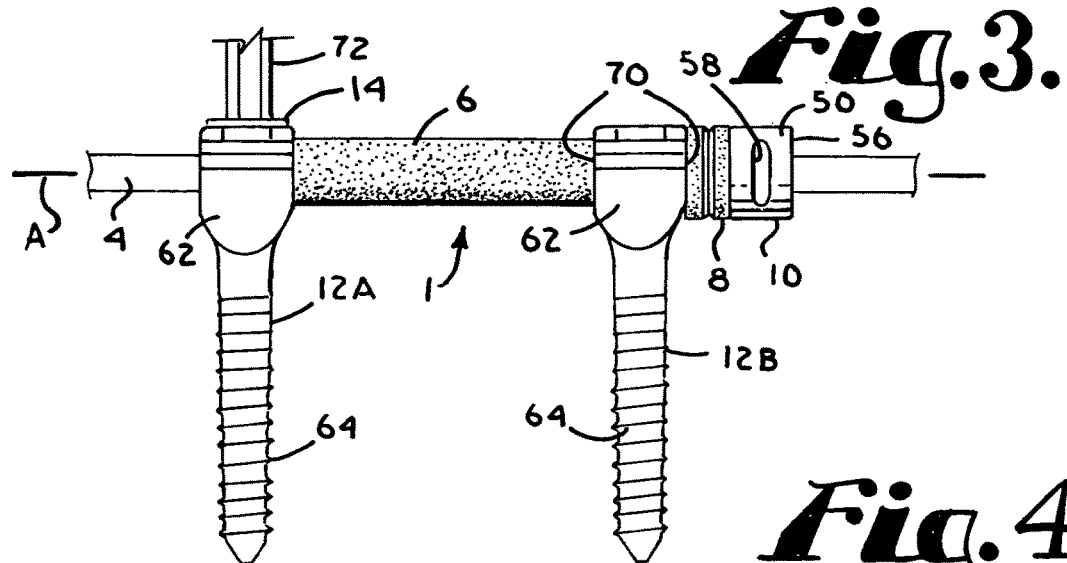
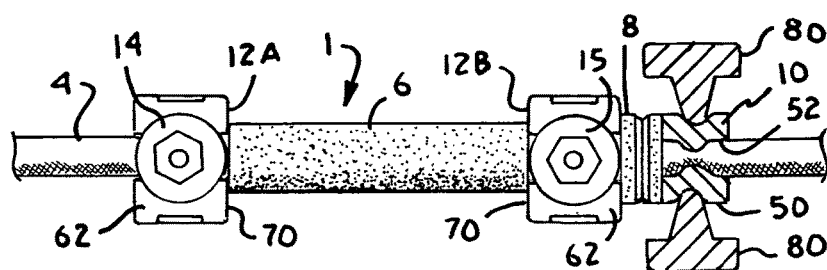
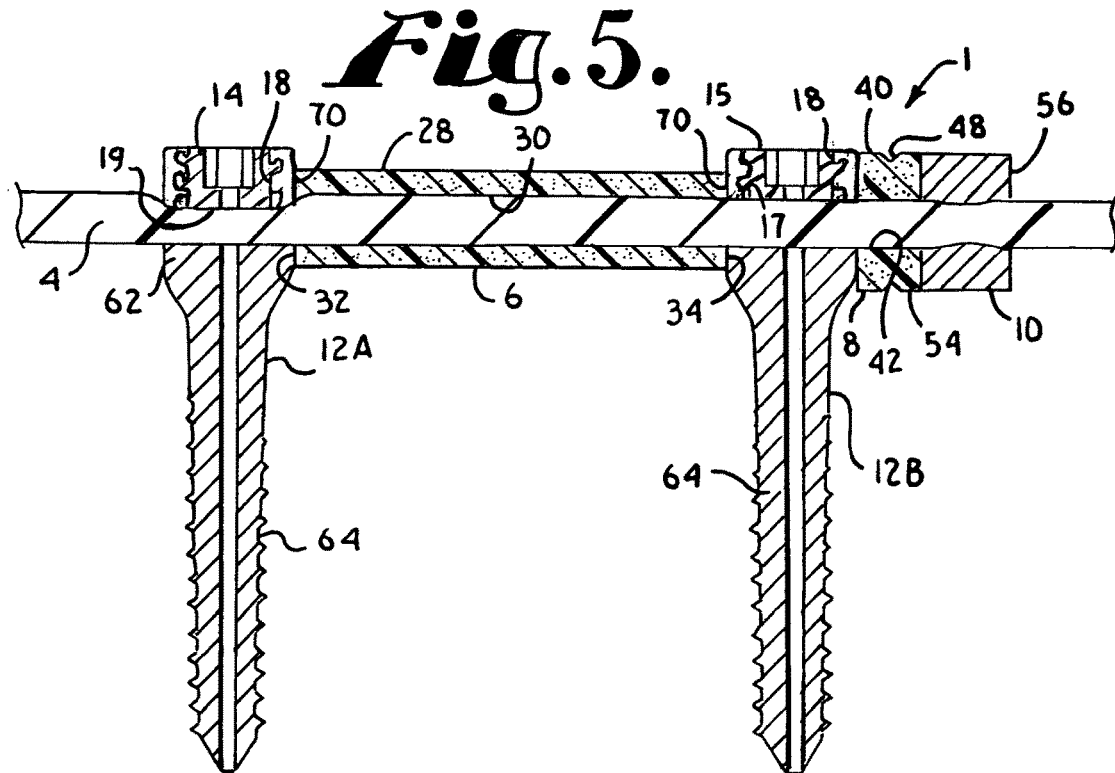

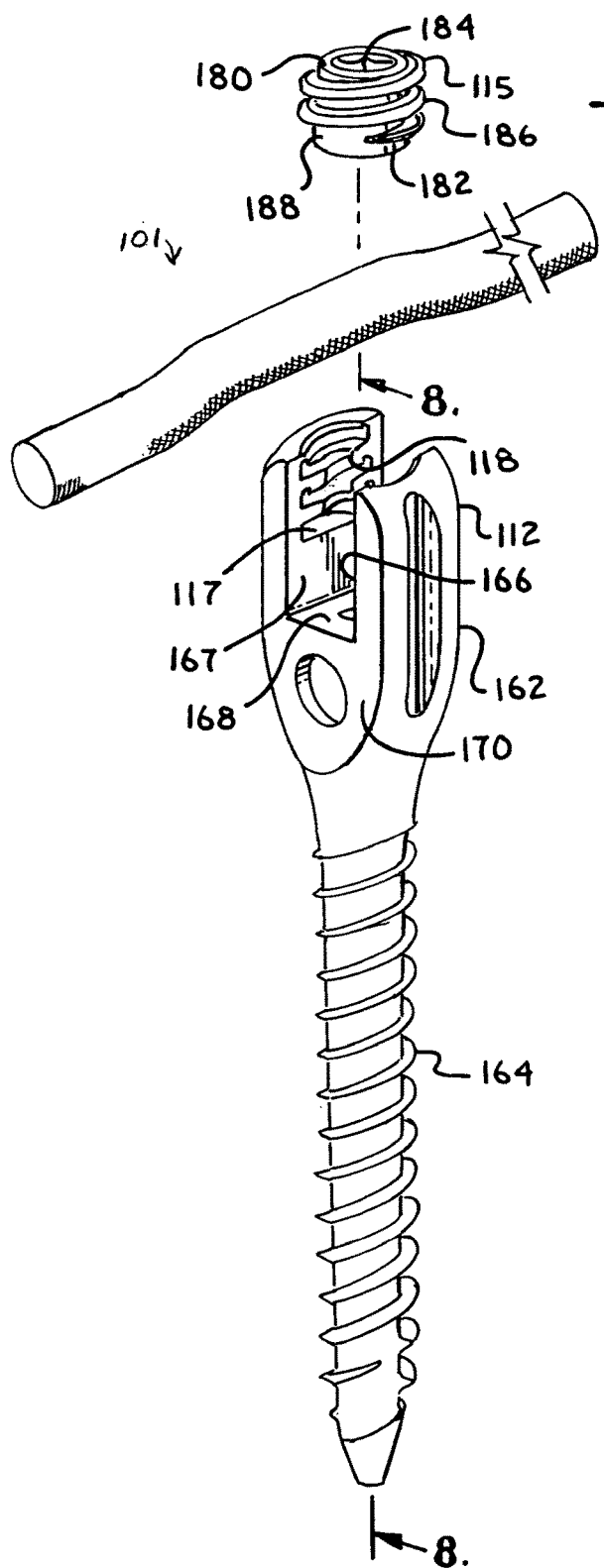
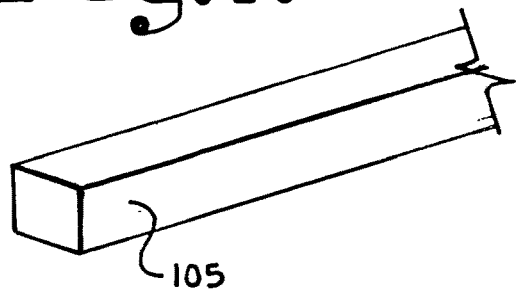

BONE ANCHOR ASSEMBLIES WITH INTERCHANGEABLE AND DIFFERENT LOCKING THREADED CLOSURES

CROSS-REFERENCE TO RELATED APPLICATIONS

This application is a continuation of U.S. patent application Ser. No. 18/332,665, filed Jun. 9, 2023, which is a continuation of U.S. patent application Ser. No. 16/380,509, filed Apr. 10, 2019, now U.S. Pat. No. 11,707,298, which is a division of U.S. patent application Ser. No. 15/389,296 filed Dec. 22, 2016, now abandoned, which is a continuation of U.S. patent application Ser. No. 12/661,042 filed Mar. 10, 2010, now abandoned, which claims the benefit of U.S. Provisional Application No. 61/210,058 filed Mar. 13, 2009. U.S. patent application Ser. No. 12/661,042 is also a Continuation-in-Part of U.S. patent application Ser. No. 12/584,980 filed Sep. 15, 2009, now U.S. Pat. No. 10,729,469, which claims the benefit of U.S. Provisional Application No. 61/192,312 filed Sep. 17, 2008. U.S. patent application Ser. No. 12/661,042 is also a Continuation-in-Part of U.S. patent application Ser. No. 12/148,465 filed Apr. 18, 2008, now U.S. Pat. No. 10,258,382, which claims the benefit of U.S. Provisional Application No. 60/927,111 filed May 1, 2007. U.S. patent application Ser. No. 12/661,042 is also a Continuation-in-Part of U.S. patent application Ser. No. 12/229,207 filed Aug. 20, 2008, now U.S. Pat. No. 8,353,932, which claims the benefit of U.S. Provisional Application No. 60/994,083 filed Sep. 17, 2007. U.S. patent application Ser. No. 12/229,207 is also a Continuation-in-Part of U.S. patent application Ser. No. 11/894,001 filed Aug. 17, 2007, now U.S. Pat. No. 8,292,926, which claims the benefit of U.S. Provisional Application No. 60/851,353 filed Oct. 12, 2006. U.S. patent application Ser. No. 12/661,042 is also a Continuation-in-Part of U.S. patent application Ser. No. 11/328,481 filed Jan. 9, 2006, now U.S. Pat. No. 7,862,587, which claims the benefit of U.S. Provisional Application No. 60/736,112 filed Nov. 10, 2005, U.S. Provisional Application No. 60/728,912 filed Oct. 21, 2005, U.S. Provisional Application No. 60/725,445 filed Oct. 11, 2005, and U.S. Provisional Application No. 60/722,300 filed Sep. 30, 2005. All of the above are fully incorporated by reference herein for all purposes.

The present invention relates to apparatuses and methods for use in performing spinal surgery and, in particular, to bone attachment structures for dynamic spinal support and alignment, preferably using minimally or less invasive techniques.

Historically, it has been common to fuse adjacent vertebrae that are placed in fixed relation by the installation there along of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexion, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

An alternative to fusion, which immobilizes at least a portion of the spine, and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Another type of soft or dynamic system known in, the art includes bone anchors connected by cords or strands. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. The cords or strands utilized in such systems typically are stretched or pulled to maximum tension, followed by fixing the cords to adjoining bone screws. A variety of specialized tools for holding and stretching the cords are required for such an operation. Although easily bendable, the cords or strands utilized in such systems do not allow for elastic distraction of the system once implanted because the cord or strand must be stretched or pulled to maximum tension in order to provide a stable, supportive system.

SUMMARY OF THE INVENTION

A dynamic stabilization assembly according to the invention for attachment to at least two bone anchors includes an elongate inner core, preferably a tensioned cord, with at least one spacer, typically in the form of an elastic spacer, surrounding the core, the core and spacer disposed between the at least two bone anchors. An elastic bumper and a fixing structure or blocker are disposed on an opposite side of one of the bone anchors, the bumper in compression by cooperation between one of the bone anchors and the blocker.

In a method of one aspect of the invention, a cord and surrounding spacer are inserted between first and second implanted bone anchors with the spacer being in contact with both of the bone anchors. The cord is fixed to the first bone anchor. A bumper and a fixing structure or blocker are threaded along the cord until the bumper abuts the second bone anchor and the blocker abuts the bumper. The cord is tensioned and the blocker is crimped or otherwise fixed to the cord, such as by a set screw, resulting in a tensioned cord with both the bumper and the spacer being in compression. The cord remains in sliding engagement with the second bone anchor, advantageously allowing for some elastic distraction of the system with elongation between the screw heads once implanted, as well as compression and bending in response to spinal flexion and extension. In other embodiments according the invention, the core cord member may be replaced by relatively hard stiff rods or bars or relatively soft, deformable or non-elastic rods or bars, or other longitudinal connecting members of different shapes and materials, including PEEK and other polymers and metal cables. Assemblies of the invention may include mono- and polyaxial open and closed screws that may be used with a first locking fastener or closure top that fixes against the core member (cord, cable, rod or bar), or alternatively with a second locking limited travel closure top that is fixed to the bone screw and captures the core (cord, cable, rod or bar) in the screw, but allows such core member to be in sliding engagement with the bone screw. In the case of a polyaxial screw, the polyaxial mechanism is configured to be locked by this second closure top while allowing the core to travel through the screw head.

Objects and Advantages of the Invention

Objects and advantages of the invention include providing lightweight, reduced volume, low profile stabilization assemblies, including at least two bone anchors and a longitudinal connecting member therebetween that comprises a core and spacer and an end bumper-blocker combination. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is a partial front elevational view, similar to FIG. 2 showing a stage of assembly of the connector and bone screws of FIG. 1, showing use of a driving tool for fixing one of the first closure tops against the cord.

FIG. 4 is a partial top plan view with portions broken away to show the detail thereof, showing use of a crimping tool in a further stage of assembly of the connector and bone screws of FIG. 1.

FIG. 5 is an enlarged and partial cross-sectional view taken along the line 5-5 of FIG. 1.

FIG. 6 is an exploded perspective view of an alternative bone screw for use with the invention of FIG. 1, shown with a cord and a cord sliding limited travel closure top.

FIG. 7 is a partial perspective view of an alternative bar for use with the bone screw and closure top of FIG. 6.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

Figure 1:
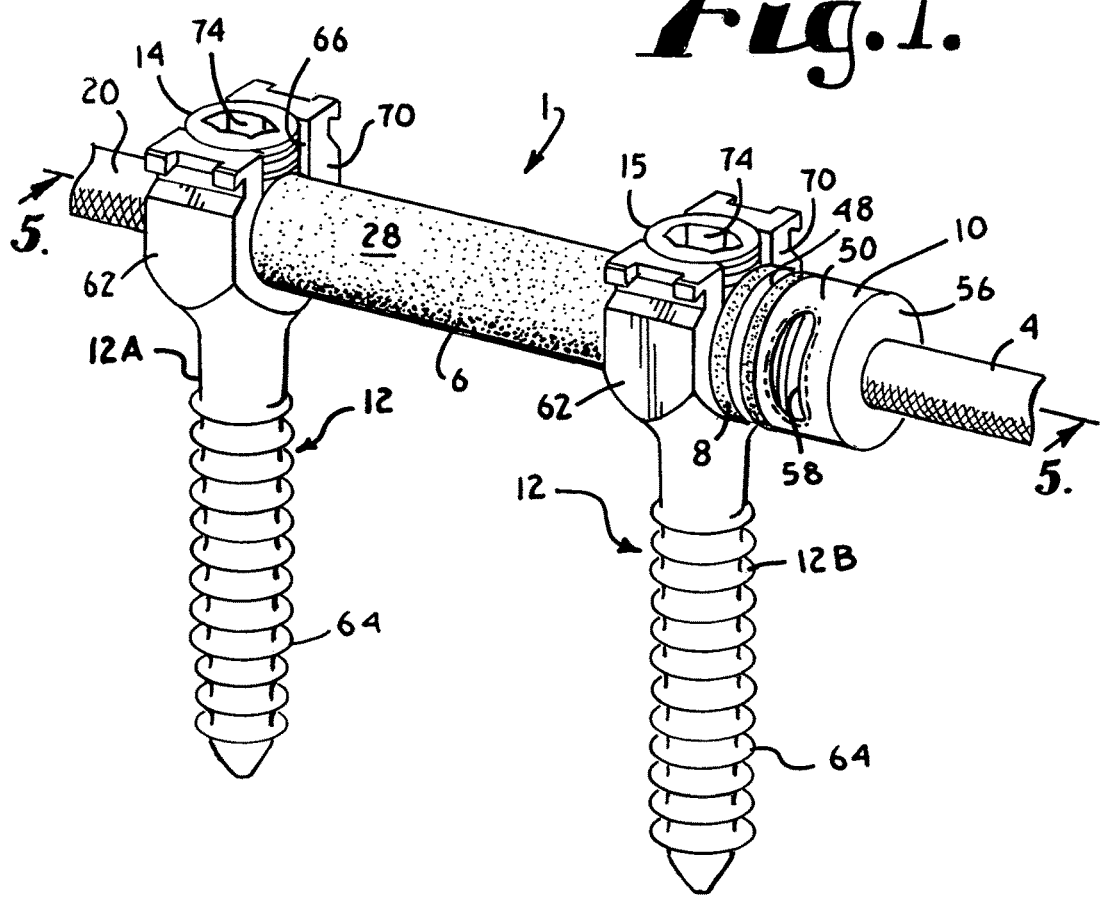
FIG. 1 is an enlarged and partial perspective view of a dynamic stabilization connector of the invention having an inner cord, an outer spacer, an elastic bumper and a fixing structure or blocker, shown as a crimping structure, the connector shown with a pair of open monoaxial bone screws, one with a cord travel or sliding closure top and one with a cord compressing and locking closure top.

With reference to FIGS. 1-5, the reference numeral 1 generally designates a non-fusion longitudinal dynamic stabilization connector assembly of the invention. The illustrated assembly 1 includes the following components: an elongate bendable and flexible core in the form of a cord 4; at least one cannulated spacer 6; an elastic bumper 8; and a fixing structure or blocking member, such as a crimping structure 10. The assembly 1 is shown with a pair of open monoaxial bone screws, generally 12, the assembly 1 extending substantially linearly along a central axis A in FIG. 3, for example. For purposes of this application, the identical bone screws 12 are identified as 12A and 12B as the one bone screw 12A cooperates with a first locking and cord pressing closure top 14 and the other bone screw 12B cooperates with a second locking limited travel closure top 15 that allows for slip or slide of the cord 4 within the bone screw 12B. The closure tops 14 and 15 are substantially similar to one another with the exception that the top 15 is sized and shaped to bottom out on a lower seating surface 17 of a run-out of an inner guide and advancement structure 18 of the bone screw 12 that mates with the outer guide and advancement structure of the closure top 14 or the closure top 15. The closure top 14 further includes an end or bottom portion 19 that extends beyond the run-out seating surface 17 and abuts against and fixes the cord to the bone screw. The guide and advancement run-out seating surface 17 is best shown and described with respect to an alternative bone screw 112 and 112' described in greater detail below with reference to FIGS. 6-14. Also, as will be described in more detail below, the bone screw 12A cooperates with the closure top 14 to fix a portion of the cord 4 to the bone screw 12A while the bone screw 12B engages and fixes the closure top 15 to the screw 12B to capture a portion of the cord 4 within the bone screw 12B, but allow for sliding movement of the cord 4 with respect to the bone screw 12B. The elongate inner cord core 4 is slidingly received within the spacer 6 and the bumper 8, and initially within the blocker or crimping structure 10, as will be described in greater detail below. The cord 4 is eventually tensioned and fixed in such tensioned state by the crimping structure 10 and the bone screw 12A. In other embodiments according to the invention, the structure 10 may include a threaded aperture (not shown) and further include a cooperating set screw in addition to or in lieu of crimping. In such embodiments, the set screw rotatably mates with the structure 10 at the threaded aperture and is rotated until a bottom surface of the screw presses against and, in some embodiments, penetrates the cord, fixing the cord within the structure 10. As will be described in greater detail below, when fully assembled and all the components are fixed in position as shown in FIGS. 1 and 5, for example, the cord 4 is in tension, the spacer 6 may be in compression or in a neutral state, and the bumper 8 is in compression.

It is noted that in other embodiments according to the invention, both the bone screws 12A and 12B may be mated with a locking limited travel closure top 15 and at least one additional blocker or crimping structure is included generally opposite the crimping structure 10 in the overall assembly to result in a cord that is tensioned along the assembly but in sliding cooperation with two or more bone anchors of such assembly. It is also noted that additional spacers 6 and bone screws 12 cooperating with closure tops 15 may be utilized according to the invention, providing longer assemblies of the invention with one of the spacers 6 placed between each bone screw and the bumper 8 and the crimping structure 10 placed at one or both ends of such assembly next to a bone screw 12 cooperating with a closure top 15 or two such closure tops 15. Also, as described in greater detail below, bone screws, spacers, bumpers and crimping structures or other blockers of the invention may be sized, shaped and used with hard or deformable rods and bars, alternatively to the cord 4.

Although the screws 12 are illustrated, it is noted that the assembly 1 may cooperate with a variety of bone screws and other bone anchors, including closed bone screws, hinged bone screws, polyaxial bone screws, with or without compression inserts, and bone hooks that may in turn cooperate with a variety of closure structures having threads, flanges, or other structure for fixing the closure structure to the bone anchor, and may include other features, for example, external or internal drives, break-off tops and inner set screws. A closed bone anchor with or without a set screw may also be used in the invention to capture the cord 4 in sliding, but not fixed engagement. The bone anchors, closure structures and the connecting member 1 are then operably incorporated in an overall spinal implant system for correcting degenerative conditions, deformities, injuries, or defects to the spinal column of a patient.

The connecting member assembly 1 is elongate, with the inner core 4 being any flexible elongate material including, but not limited to cords, threads, strings, bands, cables or fibers that may be single or multiple strands, including twisted, braided or plaited materials. The illustrated cord 4 has a substantially uniform body 20 of substantially circular cross-section, a first end 22 and an opposed second end 24, the cord 4 being cut to length as required by the surgeon. Initially, the cord 4 is typically of a length longer than shown in the drawings to allow for gripping of the cord 4 during assembly with the other components of the assembly 1 and also for tensioning and attachment to the bone screws 12A and 12B as will be described in greater detail below. The cord 4 may be made from a variety of materials, including polyester or other plastic fibers, strands or threads, such as polyethylene-terephthalate. The cord 4 may be placed under axial tension prior to final installation between the bone screws 12A and 12B, for example by being tensioned along the axis A for a selected time to lengthen and otherwise deform the cord 4 during a primary creep stage. After the cord 4 reaches a secondary or steady-state creep, further tension is placed on the cord 4 in preparation for fixing between the bone screw 12A and the crimping structure 10 as will be described in greater detail below. It is noted that the cord 4 typically does not illustrate elastic properties, such as any significant additional lengthening with axial traction, after the assembly 1 is operatively assembled within a human body, but the elastic bumper 8 will allow for relative movement between the fully stretched cord 4 and the bone screw 12B in response to spinal flexion, extension and any movement that may draw the bone screw 12B away from the bone screw 12A.

Figure 2:
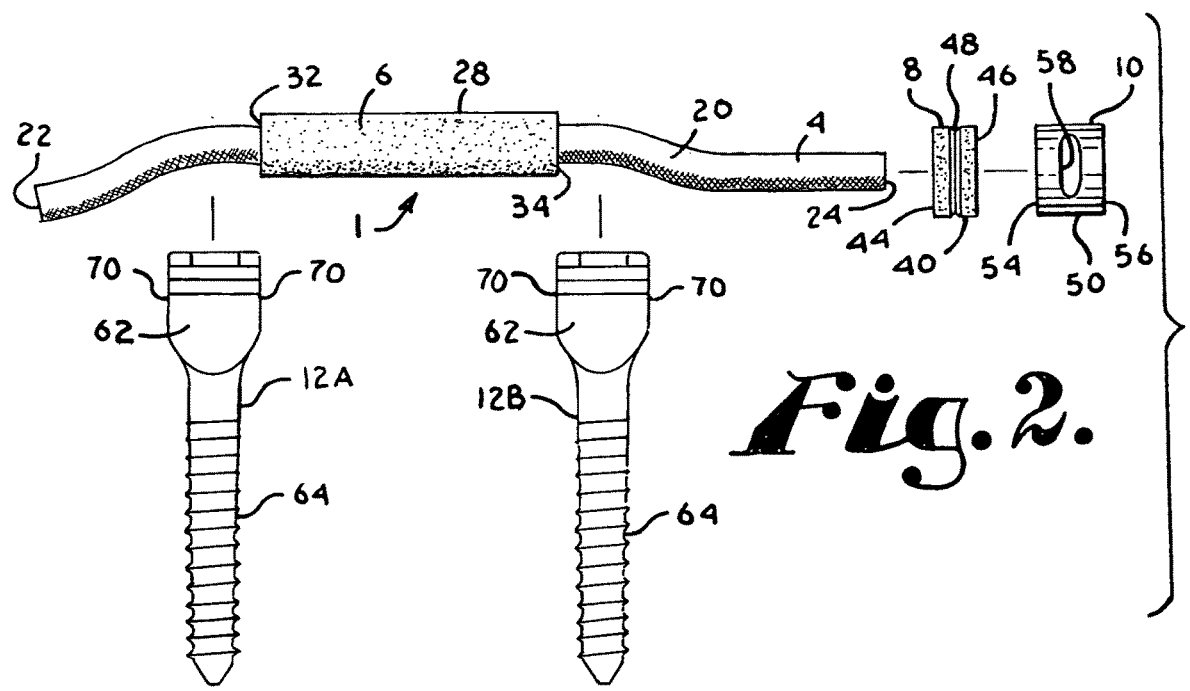
FIG. 2 is a partial and reduced and exploded front elevational view of the connector and bone screws of FIG. 1, shown without the closure tops.

With particular reference to FIGS. 1, 2 and 5, the spacer 6 is sized and shaped to be slidingly received over the cord 4 and may be made from a variety of elastic and more rigid materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the spacer 6 inner and side surfaces may be coated with an ultra-thin, ultra hard, ultra slick and ultra-smooth coating, such as may be obtained from ion bonding techniques and/or other gas or chemical treatments. The illustrated spacer 6 has an external substantially cylindrical outer surface 28 and an internal substantially cylindrical surface 30. The surface 30 is sized and shaped to closely cooperate and fit about the cord 4 and yet allow some sliding movement of the cord 4 with respect to the spacer 6 along the axis A. The spacer 6 includes opposed substantially planar and annular end surfaces 32 and 34 that are sized and shaped to abut against planar surfaces of the bone screws 12A and 12B, respectively. When initially assembled with the other components of the connecting member assembly 1, the surfaces 32 and 34 are substantially perpendicular to the axis A. It is foreseen that in some embodiments, the spacer 6 may be of smaller or larger outer circular cross section, or of a square, rectangular or other inner or outer cross-section including other curved or polygonal shapes. The spacer 6 may further include one or more compression grooves that allow for some additional compression of the spacer 6 when pressed upon in an axial direction between the bone anchors 12A and 12B. Typically, such a compression groove is substantially uniform and circular in cross-section, being formed in the external surface 28 and extending radially toward the internal surface 30. The spacer can have an off-axial lumen.

Also with particular reference to FIGS. 1, 2 and 5, the elastic bumper 8 is annular and includes an outer cylindrical surface 40, an inner cylindrical surface 42, an end surface 44 and an opposed end surface 46. The illustrated bumper 8 further includes a compression groove 48 that allows for some additional compression of the bumper 8 when pressed upon in an axial direction A between the bone anchor 12B and the crimping ring 10. The compression groove 48 is substantially uniform and circular in cross-section, being formed in the external surface 40 and extending radially toward the internal surface 42. Bumpers of the invention may include one, none or a plurality of compression grooves. The inner cylindrical surface 42 forms a bore sized and shaped for closely receiving the cord 4 therethrough as shown, for example, in FIG. 5. The end surfaces 44 and 46 are substantially parallel to one another, but can also be non-parallel.

The bumper 8 may be made from a variety of elastic materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. The bumper 8 is typically shorter in length and more elastic than the spacer 6, but may be equal to or longer than the spacer and of the same, greater or lesser durometer than the spacer 6. In order to have low or no wear debris, the bumper 8 inner and side surfaces may also be coated with an ultra-thin, ultra hard, ultra slick and ultra-smooth coating, such as may be obtained from ion bonding techniques and/or other gas or chemical treatments.

The fixing structure or blocker, illustrated as the crimping structure or ring 10 is substantially cylindrical and includes an outer surface 50 and an inner surface 52 forming a substantially cylindrical through bore that opens at planar end surfaces 54 and 56 and operatively extends along the axis A. The crimping ring 10 is sized and shaped to receive the elongate cord 4 through the inner surface 52. The crimping ring 10 further includes a pair of opposed crimp or compression grooves 58 that are pressable and deformable inwardly toward the axis A upon tensioning of the cord 4 and pre-compression of the bumper 8 during assembly of the assembly 1. The crimping ring 10 is preferably made from a stiff, but deformable material, including metals and metal alloys. It is foreseen that in lieu of or addition to the crimping surface, the blocker could include a threaded aperture and a mating locking set screw for engaging and pressing into the cord 4.

The bone screws generally 12, and in particular the illustrated screws 12A and 12B are open, fixed, monoaxial screws, each having an upper cord receiving portion 62 integral with a threaded bone attachment portion or shank 64. The portion 62 further includes a substantially U-shaped channel 66 for closely receiving the cord 4 therethrough, the channel 66 further having an upper closure top receiving portion with the helically wound guide and advancement structure 18 thereon for receiving and mating with the closure top 14 or the closure top 15. The upper, receiving portion 62 further includes opposed, substantially parallel side surfaces 70 that abut against side surfaces of the spacer 6 or the bumper 8. However, it is foreseen that according to the invention, other embodiments of the invention may include side surfaces 70 that angle away or towards one another for lordosing or kyphosing controlling embodiments as previously described in applicant's application U.S. Ser. No. 11/328,481, incorporated by reference herein.

To provide a biologically active interface with the bone, the threaded shanks 64 of the bone screws 12A and 12B may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca3(PO_4)_2$), tetra-calcium phosphate ($Ca_4P_2O_9$), amorphous calcium phosphate and hydroxyapatite ($C_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1, 2 and 5, the closure structures 14 and 15 can be any of a variety of different types of closure structures for use in conjunction with the present invention with suitable mating structure on the interior surface of the receiver 62 of the open bone screws 12. The illustrated closure structures 14 and 15 are each rotatable between the spaced arms forming the receiver 62 and are substantially cylindrical, including an outer helically wound guide and advancement structure in the form of a flange form that operably joins with the guide and advancement structure 18. A driving tool 72 illustrated in FIG. 3 is sized and shaped for engagement with an internal drive feature 74 and is used for both rotatable engagement and, if needed, disengagement of the closure 14 and/or closure 15 from one of the receivers 62. The internal drive feature 74 may take a variety of forms and may include, but is not limited to, a hex shape (as shown), TORX or other features or apertures, such as slotted, tri-wing, spanner, two or more apertures of various shapes, and the like. As stated above, the closure 14 and the closure 15 are substantially identical with the exception of a height or depth dimension in the form of the portion or knob 19 that extends operatively perpendicular to the axis A. The closure structure 14 that includes the portion 19 is sized and shaped to be long enough to compress against the cord 4 and frictionally fix the cord 4 in the receiver 62 when fully seated and mated with the guide and advancement structure 18. (See, e.g., FIG. 14 that shows a similar closure 114 that abuts against a run-out seat 117' and has an extended portion 119 for pressing down on a core, such as a cord or rod or bar). The illustrated closure top 14 may further include points or projections for piercing into the cord 4 to provide enhanced contact and fixing of the cord 4 to the receiver 62. The closure 15 is sized and shaped to be long enough to fully seat within the receiver 62 and mate with the guide and advancement structure 18 run-out seating surface 17 in order to fix the closure 15 in the bone screw and capture the cord 4 within the receiver 62. However, the closure 15 is too short to fix the cord 4 against the receiver 62. Rather, when the closure 15 is fully seated and mated in the receiver 62, the cord 4 remains in slidable relationship with the bone screw 12B and is not fixed against a surface of the receiver 62. (See, e.g., FIG. 9 that shows a similar closure 115 that abuts against a run-out seat 117 and is spaced from or in sliding engagement with a core, such as a cord or cable or rod or bar).

In use, the two bone screws 10 and 12 are implanted into vertebrae for use with the dynamic connecting member 1. Each vertebra may be pre-drilled to minimize stressing the bone. Furthermore, if a cannulated bone screw shank and/or closure top is utilized (as illustrated), each vertebra will have a guide wire or pin (not shown) inserted therein that is shaped for the bone screw cannula of the bone screw shank 64 and provides a guide for the placement and angle of the shank 64 with respect to the cooperating vertebra. A further tap hole may be made and the shank 64 is then driven into the vertebra by rotation of a driving tool (not shown) that engages a driving feature on or near the top portion 62 of the screw 12. It is foreseen that the screws 12A and 12B and the dynamic connector 1 can be inserted in a percutaneous or minimally invasive surgical manner.

With particular reference to FIGS. 2-4, the dynamic connector assembly 1 is assembled by inserting the cord 4 into the through bore formed by the internal surface 30 of the spacer 6. Also as indicated in FIGS. 2 and 3, the cord 4 is first received into the U-shaped opening 66 of the open bone screw 12A and the U-shaped opening 66 of the bone screw 12B, with the spacer 6 being disposed between facing surfaces 70 of bone screws 12A and 12B. The closure top 14 is rotated and driven into the receiver 62 of the bone screw 12A until the closure top 14 frictionally engages the cord 4 and fixes the cord 4 to the screw 12A. Before or after the closure top 14 is tightened, the closure top 15 may be inserted and rotated into the receiver 62 of the bone screw 12B until the top 15 is fully seated and engaged with such receiver run-out surface 17, capturing but not fixing the cord 4 to the bone screw 12B. The bumper 8 is threaded along the cord 4 with the cord sliding through the through-bore formed by the inner surface 42 until the bumper face 44 abuts against the surface 70 of the bone screw 12B located opposite the spacer 6. The crimping structure 10 is threaded along the cord 4 with the cord sliding through the through-bore formed by the inner surface 52 until the crimper face 54 abuts against the bumper face 46.

The cord 4 is tensioned and the bumper 8 is compressed against the bone screw 12B by axial movement of the crimping structure 10 against the bumper 8, squeezing the bumper 8 between the bone screw 12B and the crimping structure 10. The spacer 6 also may be compressed at this time. With particular reference to FIG. 4, a crimping tool 80 is used to frictionally attach the tensioned cord 4 to the crimping structure 10, thereby holding the cord 4 in tension between the bone screw 12A and the crimping structure 10 and also compressing the bumper 8 against the bone screw 12B.

The resulting connecting member assembly 1 is loaded with the cord 4 in tension and the bumper 8 and optionally the spacer 6 in compression. The assembly 1 is thus substantially dynamically loaded and oriented relative to the cooperating vertebra, providing relief (e.g., shock absorption) and protected movement in response to spinal flexion and extension, and further responding to distractive or tensioning forces as well as to compressive forces.

If removal of the dynamic connector assembly 1 from the bone screws 12A and/or 12B is necessary, or if it is desired to release the assembly 1 at a particular location, disassembly is accomplished by using the driving tool 72 with a driving formation cooperating with the closure tops 14 and 15 to rotate and remove the closure top from the bone screw 12A and/or 12B. Disassembly is then accomplished in reverse order to the procedure described previously herein for assembly.

With reference to FIGS. 6-9, a bone screw 112 is illustrated that is identical to the bone screw 12 of the assembly 1 with the exception that the U-shaped channel 66 formed by inner surfaces of the screw 12 has been replaced with a substantially rectangular channel 166 formed by opposed planar surfaces 167 and a bottom planar surface 168. The bone screw 112 has a receiver 162 and a shank 164, the receiver 162 having a discontinuous guide and advancement structure 118 that is formed in the opposed surfaces 167. The bone screw 112 may be utilized in an assembly 101 substantially similar to the assembly 1 that includes a cord 104 identical or substantially similar to the cord 4 and further includes the spacer 6, elastic bumper 8, crimping structure 10 of the assembly 1 previously described herein. Because of the squared off shape of the channel 166, the bone screw 112 may also be readily used with other longitudinal connecting members, such as the bar 105 shown in FIG. 7 and the rod 106 shown in FIG. 10. The bar 105 and the rod 106 may be made of a variety of materials ranging from deformable plastics to hard metals, depending upon the desired application. Thus, bars and rods of the invention may be made of materials including, but not limited to metal, metal alloys or other suitable materials, plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. Whether the longitudinal connecting member of the invention is a cord, rod or bar; hard-surfaced or soft and deformable; or elastic or non-elastic, the combination of a limited travel closure top that allows the connecting member some movement within the bone screw further cooperating with a bumper and a connector holding structure such as the crimping structure 10, advantageously allows for limited movement of the connector with respect to the bone screw, creating a dynamic connection between spinal assembly and cooperating vertebrae.

Figure 8:
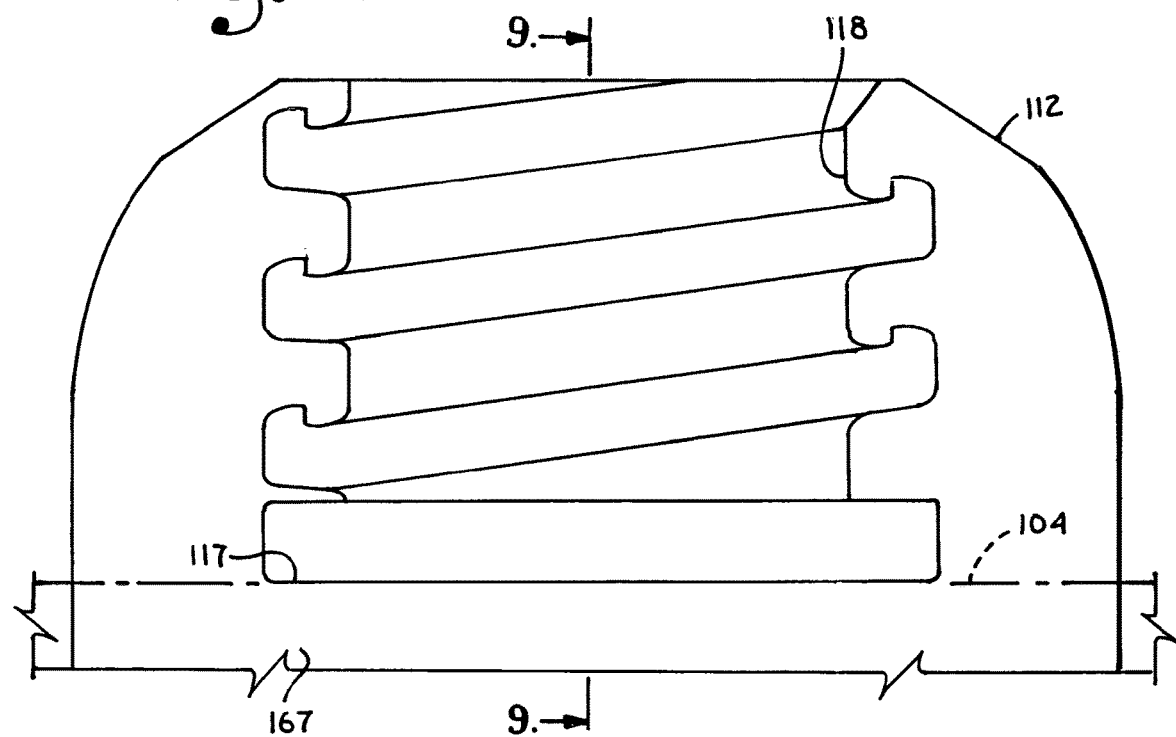
FIG. 8 is an enlarged and partial cross-sectional view of the bone screw of FIG. 6 taken along the line 8-8 of FIG. 6 and showing a portion of the cord in phantom.
Figure 9:
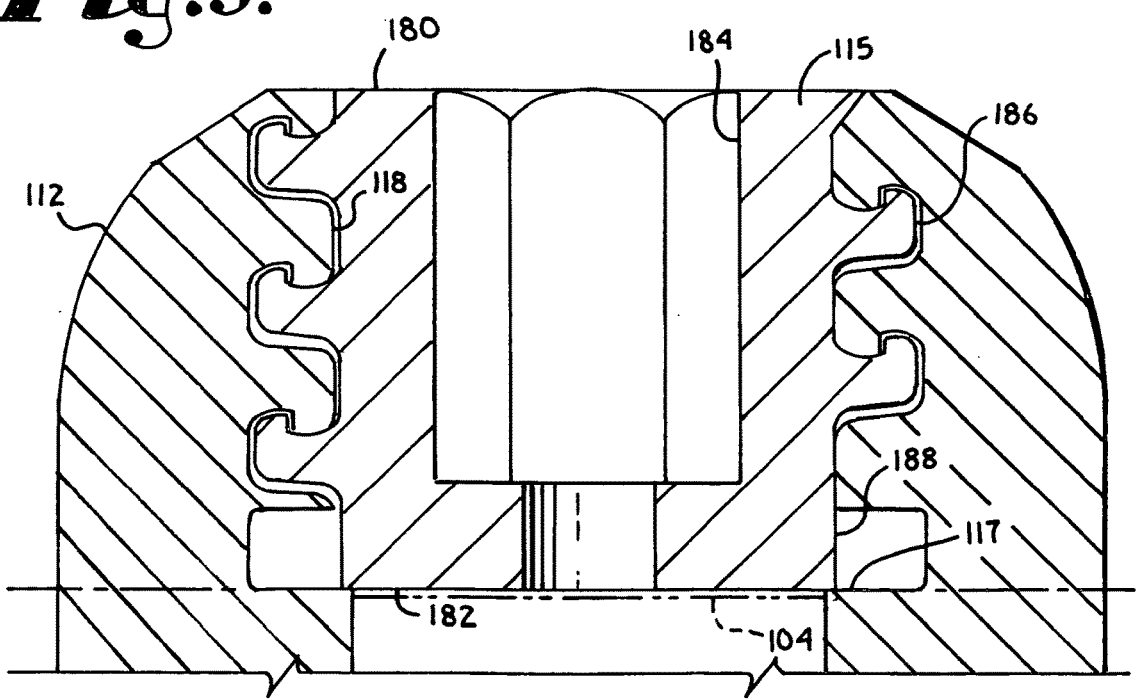
FIG. 9 is an enlarged and partial cross-sectional view taken along the line 9-9 of FIG. 8 and also showing the mated closure top in cross section and a portion of the cord in phantom.
Figure 10:
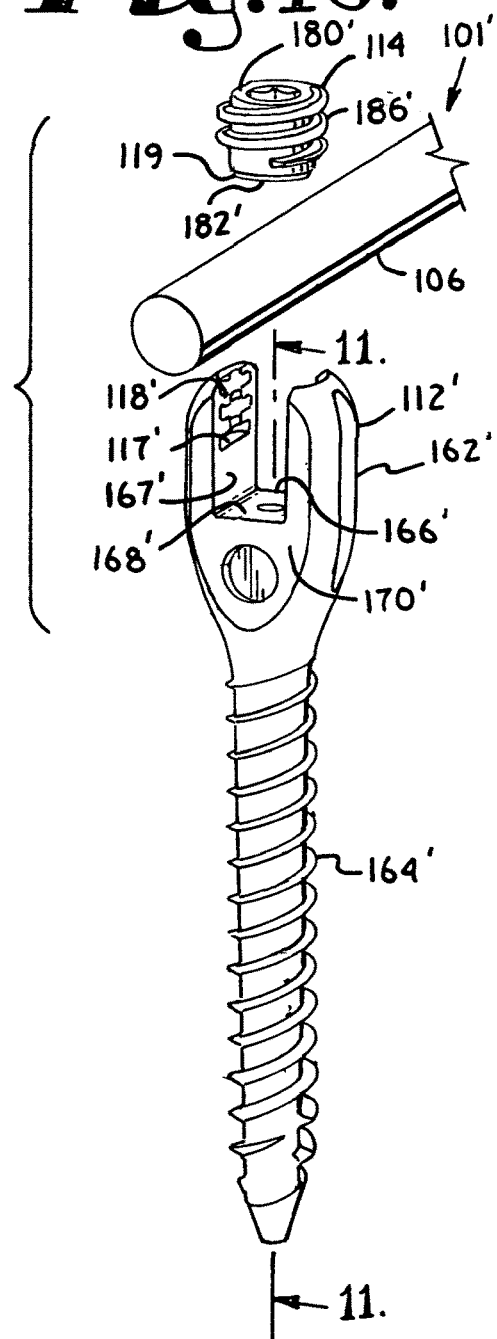
FIG. 10 is an exploded perspective view of the bone screw of FIG. 6 shown with a second locking closure top and a deformable rod.
Figure 11:
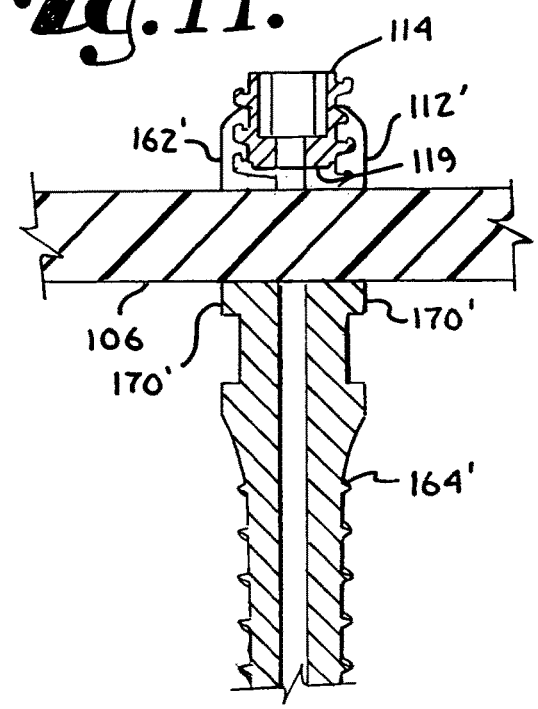
FIG. 11 is a partial cross-sectional view taken along the line 11-11 of FIG. 10 and showing the second locking closure top in an early stage of assembly.

With particular reference to FIGS. 8 and 9, the bone screw 112 guide and advancement structure 118 that receives and mates with the limited travel closure 115 includes a run-out aperture or groove partially defined by a bottom or lower seating surface 117 sized and shaped for frictional engagement with a portion of the closure 115. As shown in FIG. 9, the closure 115 minor diameter is slightly bigger than the run-out groove so the closure 115 abuts against the surface 117 when driven downward into the receiver. The seating surface 117 terminates at the opposed planar surfaces 167.

The bone screw receiver 162 further includes opposed, substantially parallel outer side surfaces 170. It is foreseen that according to the invention, other embodiments of the invention may include side surfaces that angle away or towards one another for lordosing or kyphosing controlling embodiments as previously described in applicant's application U.S. Ser. No. 11/328,481, the disclosure of which is incorporated by reference herein. It is also noted that the bone screw 112 is identical or substantially similar to the bone screws described in described in detail in Applicant's U.S. patent application Ser. No. 12/584,980, the disclosure of which is incorporated by reference herein.

Specifically, the closure top 115 is substantially cylindrical and includes a top surface 180, a bottom surface 182, a drive feature 184 formed in the top surface 180 and an outer guide and advancement structure 186 sized and shaped to mate with the guide and advancement structure 118 of the bone screw 112. A cylindrical surface 188 represents the minor diameter of a major portion of the closure 115. The illustrated closure top 115 is rotatable between the spaced arms forming the receiver 162 of the screw 112. The illustrated helically wound guide and advancement structure 186 is in the form of a flange form that operably joins with respective guide and advancement structure 118. A driving tool or tools (not shown) sized and shaped for engagement with the internal drive feature 184 is used for both rotatable engagement and, if needed, disengagement of the closure 115 from the screw 112. The internal drive feature 184 may take a variety of forms and may include, but is not limited to, a hex shape, TORX or other features or apertures, such as slotted, tri-wing, spanner, two or more apertures of various shapes, and the like.

With particular reference to FIG. 9, the closure top 115 is sized and shaped to cooperate with the run-out surface 117 to lock the closure 115 on the bone screw 112 independent of any pressure being placed by the closure 115 on the cord 104. Due to the size of the surface 188, the bottom surface 182 near the surface 188 forms a radially extending shelf or abutment seat. When the closure 115 is tightened by rotation into the screw 112, the bottom 182 abuts against the surface 117, allowing the closure to be tightened in the screw receiver 162 independent of whatever size cord 104 or other core, such as the bar 105 might be. Stated in another way, the closure 115 is prohibited from entering the space between the planar surfaces 167 that support the cord 104 or other core therebetween. Thus, it is not possible for the closure 115 to press upon the cord 104, allowing such cord to slide between the closure top 115 and the surfaces 167 and 168.

With reference to FIGS. 10-14, a bone screw 112' is illustrated that is identical to the bone screw 112, having a receiver 162', a shank 164', a rectangular channel 166' formed by opposed planar surfaces 167' and a bottom surface 168', the same or substantially similar to the receiver 162, shank 164, channel 166, opposed planar surfaces 167 and bottom surface 168 previously described herein with respect to the bone screw 112. Further, the bone screw 112' includes a lower seat 117' of a guide and advancement structure 118' and side surfaces 170', the same or similar to the lower seat 117, guide and advancement structure 118 and side surfaces 170 of the bone screw 112. The bone screw 112 is shown with the plastic, deformable rod 106 and a locking closure top 114 having a lower extension portion 119 that is the same or similar to the closure top 14 having the extended bottom portion 19 previously described herein with respect to the assembly 1.

The closure top 114 is substantially cylindrical and includes a top surface 180', a bottom surface 182', a drive feature 184' formed in the top surface 180' and an outer guide and advancement structure 186' sized and shaped to mate with the guide and advancement structure 118' of the bone screw 112'. A cylindrical surface 188' represents the minor diameter of a major portion of the closure 114. The illustrated closure top 114 is rotatable between the spaced arms forming the receiver 162' of the screw 112'. The illustrated helically wound guide and advancement structure 186' is in the form of a flange form that operably joins with respective guide and advancement structure 118'. A driving tool or tools (not shown) sized and shaped for engagement with the internal drive feature 184' is used for both rotatable engagement and, if needed, disengagement of the closure 115 from the screw 112. The internal drive feature 184 may take a variety of forms and may include, but is not limited to, a hex shape, TORX or other features or apertures, such as slotted, tri-wing, spanner, two or more apertures of various shapes, and the like.

Figure 12:
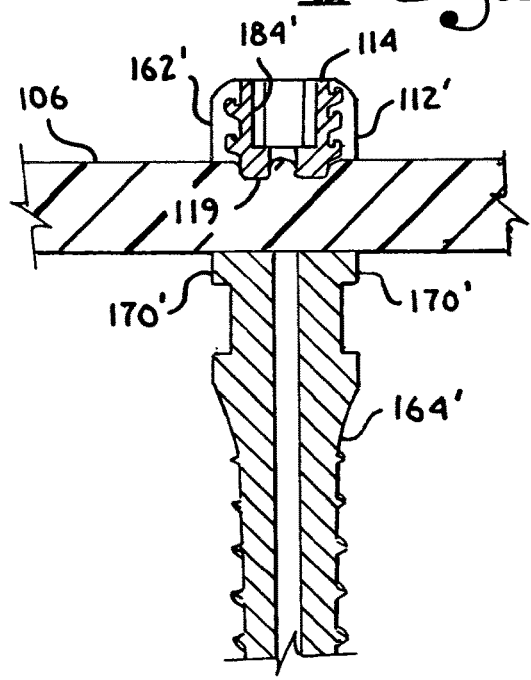
FIG. 12 is a partial cross-sectional view, similar to FIG. 11, showing the second closure top fully assembled within the bone screw and engaged with and compressing a deformable rod.
Figure 13:
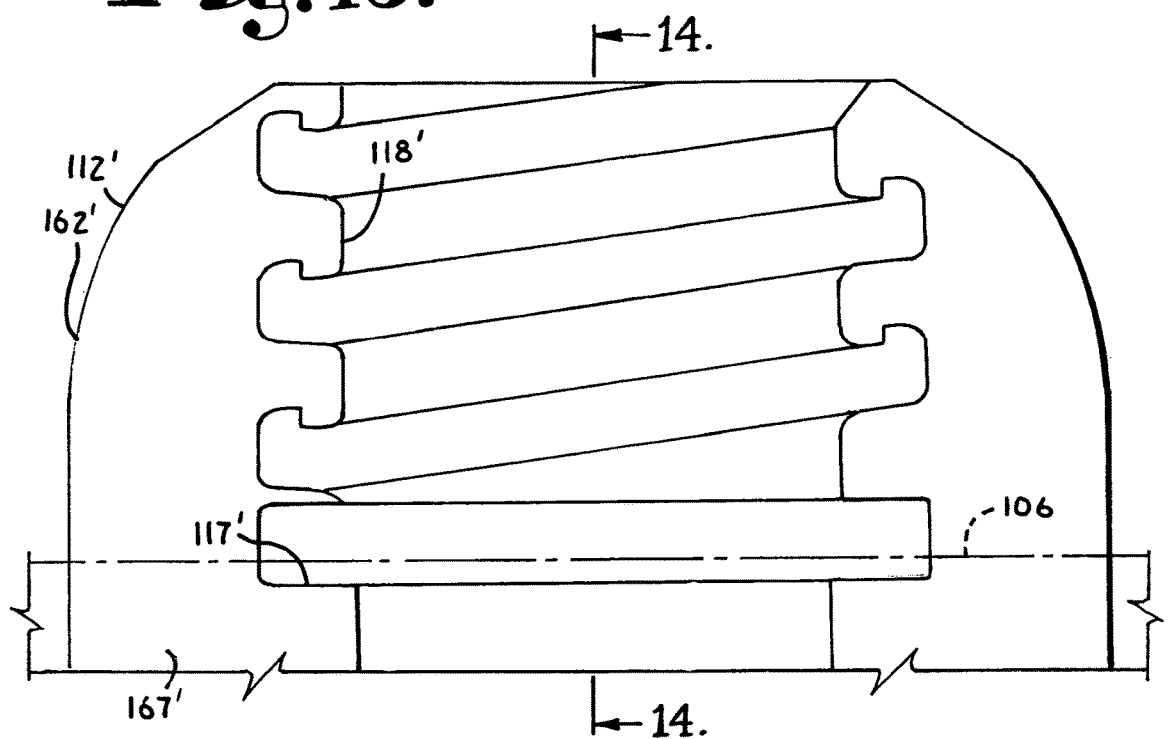
FIG. 13 is an enlarged and partial cross-sectional view of the bone screw of FIG. 10 taken along the line 11-11, with a portion of the deformable rod being shown in phantom.
Figure 14:
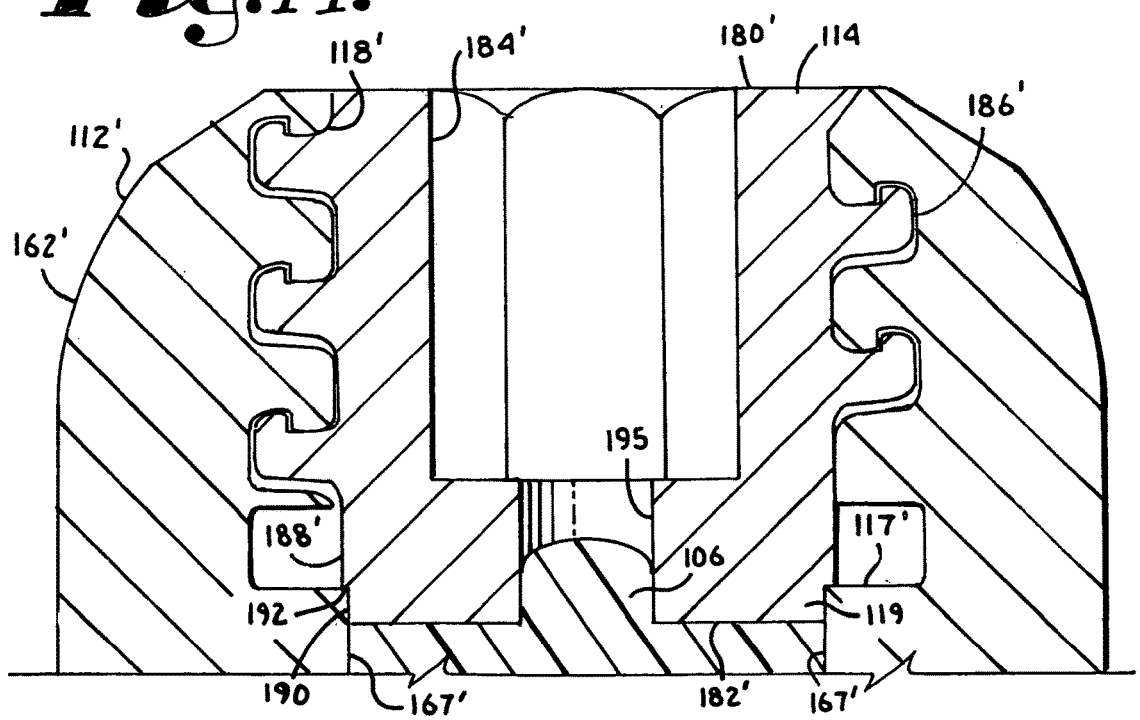
FIG. 14 is an enlarged and partial cross-sectional view, taken along the line 14-14 of FIG. 13, also showing the mated closure top and a portion of the deformable rod in cross-section.

With particular reference to FIG. 14, the closure top 114 is sized and shaped to cooperate with the run-out surface of the guide and advancement structure 118' to lock the closure 114 on the bone screw 112' independent of any pressure being placed by the closure 114 on the deformable rod 106. In the illustrated embodiment, the closure 114 includes a second cylindrical surface 190 located adjacent to and below the surface 188' that defines the minor diameter of most of the closure 114. The second cylindrical surface 190 has a second diameter smaller than the minor diameter of the surface 188'. The outer surface 190 partially defines the extended portion 119. The surface 190 is located near the bottom surface 182' of the closure 114 that contacts and presses against the deformable rod 106 or other longitudinal connecting member core located within the bone screw receiver 162' during operation. As shown in FIGS. 12 and 14, the portion 119 presses against and partially deforms the rod 106. A radially extending shelf or abutment seat 192 is formed between the cylindrical surface 188' and the cylindrical surface 190. When the closure 114 is tightened by rotation into the screw 112', the seat 192 abuts against the surface 117', allowing the closure to be tightened in the screw receiver 162' independent of the rod 106. The rod 106 is pressed upon and held in place by the bottom surface 182' of the screw, with some deformation of the rod 106 being acceptable and even desirable. In the illustrated embodiment, some of the rod material is allowed to flow up into an inner bore 195 of the closure 114. However, because of the cooperation between the seat 192 and the screw surface 117', the rod 106 is protected against over-deformation or crushing that might lead to instability and failure. Furthermore, if the rod 106 exhibits creep or other deformation during operation, loosening or lessening of the contact engagement between the closure bottom surface 182' and the rod 106 will not result in loosening of the closure 114 from the screw 112'.

Figure 15:
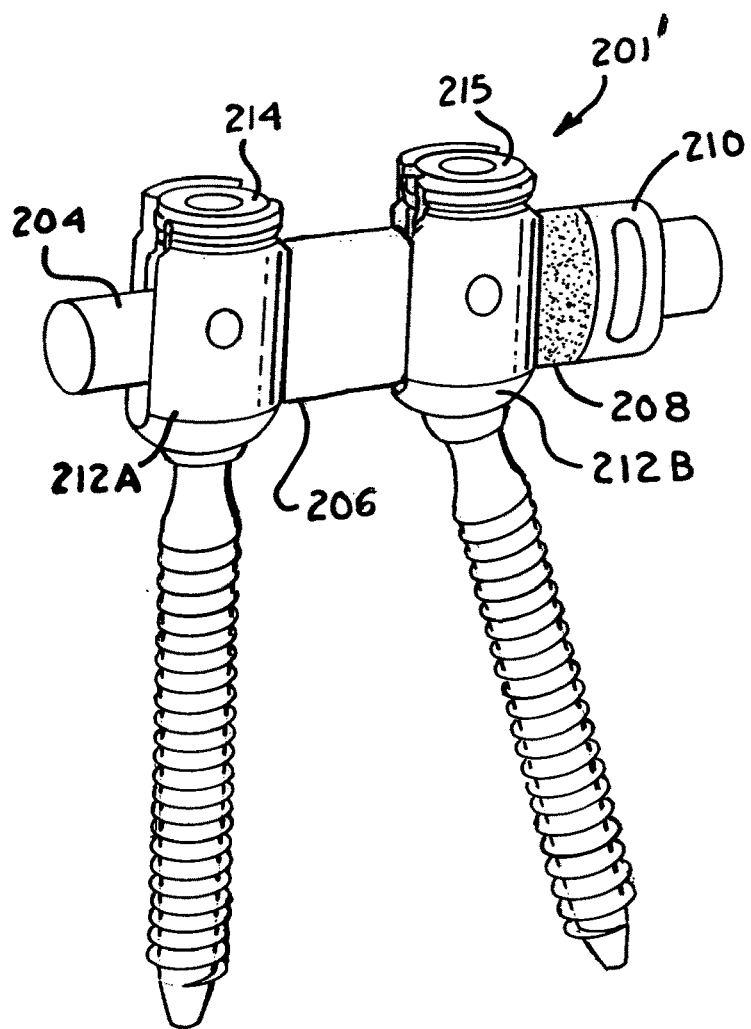
FIG. 15 is a perspective view of another alternative embodiment of a dynamic stabilization connector of the invention having an inner rod, an elastic bumper and a blocking structure, the connector shown with a pair of open polyaxial bone screws.
Figure 16:
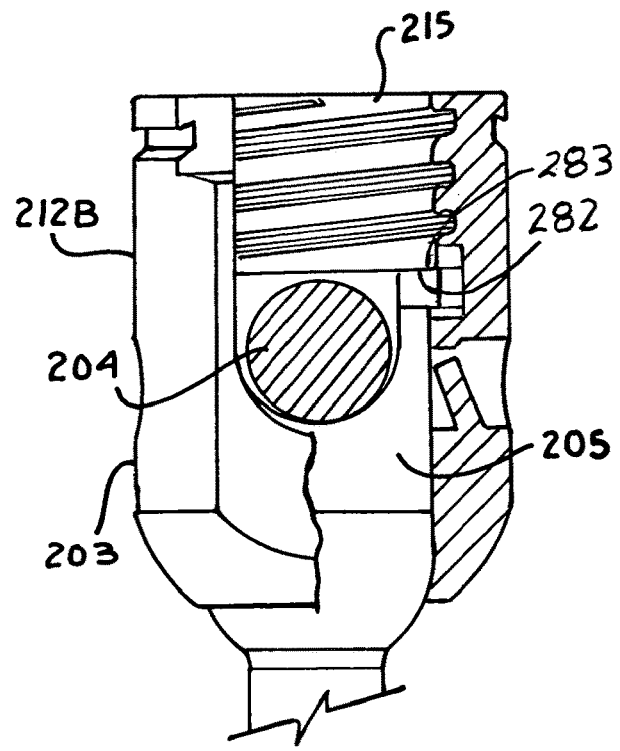
FIG. 16 is an enlarged and partial side elevational view of one of the bone screws of the embodiment of FIG. 15 with portions broken away to show the detail thereof.

With reference to FIGS. 15 and 16, an assembly 201' according to the invention is illustrated that provides for dynamic stabilization similar to the assembly 1 utilizing polyaxial bone screws. The illustrated assembly 201 includes a solid, hard-surfaced rod 204, a spacer 206, an elastic bumper 208, a crimping structure 210 and a pair of polyaxial bone screws 212A and 212B. The bone screws 212A and 212B are identical or substantially similar to those described in Applicant's U.S. patent application Ser. No. 12/229,207, filed Aug. 20, 2008 entitled "Polyaxial Bone Anchor Assembly With One-Piece Closure, Pressure Insert and Plastic Elongate Member," (hereafter, the '207 application), the disclosure of which is incorporated by reference herein. A closure top 214 fixes the rod 204 in the bone screw 212A and a closure top 215 captures the rod 204 in the bone screw 212B, but a bottom surface 282 thereof does not fix the rod 204 with respect to the bone screw 212B as illustrated in FIG. 16. (See, e.g., FIGS. 15-18 of the '207 application for illustrations of fixing of a rigid or deformable rod with a bone screw the same or similar to the screw 212A). Each screw 212A and 212B further includes a receiver 203 for slidingly pivotally receiving a bone screw shank upper portion, and a lower pressure insert 205 having surfaces for engaging the shank upper portion and surfaces for closely receiving the rod 204. With reference to FIG. 16, the closure top 215 lower surface 282 engages upper arm surfaces 283 of the pressure insert 205 to capture the rod 204 and lock the polyaxial mechanism of the bone screw 212B. Thus, the captured rod 204 is in sliding engagement with the screw 212B. The spacer 206, elastic bumper 208 and the crimping structure 210 are the same or similar in form and function to the spacer 6, bumper 8 and crimping structure 10 previously described herein with respect to the assembly 1, with the crimping structure 210 directly engaging the rod 204. In alternative embodiments, a cord or deformable rod may be utilized in lieu of the illustrated rigid rod 204. The pressure insert 205 may also be configured to receive a square or rectangular bar.

It is to be understood that while certain forms of the present invention have been illustrated and described herein, it is not to be limited to the specific forms or arrangement of parts described and shown.

What is claimed is:

1. A receiver assembly for capturing a connecting member in a receiver of the receiver assembly via a first threaded closure and second threaded closure that are interchangeable for different locking configurations in the receiver assembly, the receiver assembly comprising:

the receiver having a central axis, a base portion, and an upper portion defining a first channel configured to receive the connecting member, the first channel extending between a front face and a back face opposite the front face of the receiver and communicating with a top surface defining a top of the receiver, the receiver having interior surfaces and exterior side surfaces opposite the interior surfaces, the interior surfaces having a helically wound receiver thread formed in at least a portion therein, the exterior side surfaces extending horizontally and radially proximate the top surface of the receiver, each front face and back face having a planar surface extending parallel relative to each other and the central axis with outer ends of each of the exterior side surfaces opening onto the planar surface on each front face and back face of the receiver, and the receiver including a lower pressure insert at least partially positionable within the first channel having upright arms forming a second channel therebetween and defining a rod seat surrounding a central opening for a tool to pass through, the upright arms extending above a top surface of the connecting member positioned in the second channel against the rod seat;

the first threaded closure configured to be positioned within the first channel to capture the connecting member in the receiver, the first threaded closure comprising a first cylindrical body with a first outer diameter having a first longitudinal axis, a first planar top surface having a first central internal drive structure with a first tool abutment surface comprising a first centralized through-bore around the first longitudinal axis, a lower surface defined in part by an inwardly positioned downward protrusion having a second outer diameter less than the first outer diameter, an external side surface on the first cylindrical body having a continuous helically wound thread configured to rotatably mate with the helically wound receiver thread, and a first bottom surface on the inwardly positioned downward protrusion communicating, the first centralized through-bore extending from the first planar top surface to the first bottom surface, the first bottom surface configured to compressively engage the connecting member positioned against the rod seat of the lower pressure insert so as to lock the receiver assembly;

the second threaded closure interchangeable with the first threaded closure configured to be positioned within the first channel for capturing the connecting member in the receiver, the second threaded closure comprising a second cylindrical body with a third outer diameter equal to the first outer diameter of the first threaded closure and having a second longitudinal axis, a second planar top surface having a second central internal drive structure with a second tool abutment surface comprising a second centralized through-bore around the second longitudinal axis, a second bottom surface with an annular outer edge adjacent a second external side surface on the second cylindrical body, the second centralized through-bore extending from the second planar top surface to the second bottom surface, the second bottom surface configured to compressively engage the upright arms of the lower pressure insert and be spaced apart from the top surface of the connecting member positioned in the second channel of the lower pressure insert, and the external side surface on the second cylindrical body having a continuous helically wound thread configured to rotatably mate with the helically wound receiver thread so as to lock the receiver assembly, wherein when the receiver assembly is in one of the different locking configurations via the first or second threaded closure in the receiver, the first or second threaded closure does not extend over any part of the top surface defining the top of the receiver.

2. The receiver assembly of claim 1, wherein the upright arms of the lower pressure insert have opposite flared out portions adjacent a top surface on each upright arm.

3. The receiver assembly of claim 1, wherein the exterior side surfaces has horizontal curvate extending instrument engaging grooves (HCEIEG) proximate the top surface of the receiver.

4. A method of capturing the connecting member in the receiver of the receiver assembly via the first threaded closure or the second threaded closure of claim 1, the method comprising:

providing the receiver;

providing the first threaded closure; and positioning the first threaded closure within the first channel of the receiver to capture the connecting member in the receiver.

5. A method of capturing the connecting member in the receiver of the receiver assembly via the first threaded closure or the second threaded closure of claim 1, the method comprising:

providing the receiver;

providing the second threaded closure; and positioning the second threaded closure within the first channel of the receiver to capture the connecting member in the receiver.

\* \* \* \* \*